(12) United States Patent
Kuramoto et al.

(10) Patent No.: US 10,195,127 B2
(45) Date of Patent: Feb. 5, 2019

(54) COSMETIC COMPOSITION

(71) Applicant: AJINOMOTO CO., INC., Tokyo (JP)

(72) Inventors: Masayuki Kuramoto, Yokkaichi (JP); Eiko Oshimura, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/851,128

(22) Filed: Sep. 11, 2015

(65) Prior Publication Data

US 2016/0000676 A1    Jan. 7, 2016

Related U.S. Application Data

(63) Continuation of application No. PCT/JP2014/056764, filed on Mar. 13, 2014.

(30) Foreign Application Priority Data

Mar. 14, 2013   (JP) .................. 2013-051479

(51) Int. Cl.

| | | |
|---|---|---|
| A61K 8/44 | (2006.01) | |
| A61K 8/92 | (2006.01) | |
| A61K 8/25 | (2006.01) | |
| A61K 8/02 | (2006.01) | |
| A61Q 19/00 | (2006.01) | |
| A61Q 1/02 | (2006.01) | |
| A61Q 1/04 | (2006.01) | |
| A61Q 1/06 | (2006.01) | |
| A61Q 1/12 | (2006.01) | |
| A61Q 17/04 | (2006.01) | |

(52) U.S. Cl.
CPC ............... *A61K 8/44* (2013.01); *A61K 8/022* (2013.01); *A61K 8/0229* (2013.01); *A61K 8/25* (2013.01); *A61K 8/92* (2013.01); *A61Q 1/02* (2013.01); *A61Q 1/04* (2013.01); *A61Q 1/06* (2013.01); *A61Q 1/12* (2013.01); *A61Q 17/04* (2013.01); *A61Q 19/00* (2013.01)

(58) Field of Classification Search
CPC .......... A61K 8/19; A61K 8/44; A61K 8/2054; A61Q 19/00; A61Q 1/02
See application file for complete search history.

(56) References Cited

U.S. PATENT DOCUMENTS

| | | | | |
|---|---|---|---|---|
| 4,640,943 A | * | 2/1987 | Meguro .................. | A61K 8/19 106/414 |
| 5,605,652 A | * | 2/1997 | Tapley .................... | A61K 8/044 106/436 |
| 6,147,148 A | | 11/2000 | Tanaka et al. | |
| 6,555,708 B1 | * | 4/2003 | Yamato .................... | A61K 8/02 401/126 |
| 6,576,695 B1 | | 6/2003 | Tanaka et al. | |
| 2011/0223223 A1 | * | 9/2011 | Murata .................... | A61K 8/31 424/401 |

FOREIGN PATENT DOCUMENTS

| | | |
|---|---|---|
| CN | 1370142 A | 9/2002 |
| CN | 1875914 A | 12/2006 |
| EP | 0 336 265 A2 | 10/1989 |
| EP | 1 207 150 A1 | 5/2002 |
| JP | 60-67406 A | 4/1985 |
| JP | 61-137808 | 6/1986 |
| JP | 1-242517 | 9/1989 |
| JP | 8-337519 | 12/1996 |
| JP | 9-323914 | 12/1997 |
| JP | 11-80561 A | 3/1999 |
| JP | 11-189674 | 7/1999 |
| JP | 2001-10928 | 1/2001 |
| JP | 2001-279129 | 10/2001 |
| WO | 01/14317 A1 | 3/2001 |

OTHER PUBLICATIONS

JP-2001-010928 Translation, "Acyl-L-Lysine powder containing . . . " accessed from: https://dossier1.j-platpat.inpit.go.jp/tri/all/odse/ODSE_GM101_Top.action printed on Mar. 2, 2017, pp. 1-16.*
Office Action dated Aug. 15, 2017 issued in corresponding Japanese patent application No. 2015-505570.
Preliminary Search Report dated May 10, 2017 in French Patent Application No. 1452146 (with English translation of Category of Cited Documents).
Combined Chinese Office Action and Search Report dated Mar. 8, 2017 in Chinese Patent Application No. 201480015253.4 (with English translation of categories of cited documents).

* cited by examiner

*Primary Examiner* — Michael G. Hartley
*Assistant Examiner* — Lance W Rider
(74) *Attorney, Agent, or Firm* — Oblon, McClelland, Maier & Neustadt, L.L.P.

(57) ABSTRACT

The present invention provides a cosmetic composition containing (A) a powder composed of one or more kinds of the N-medium-chain-acyl basic amino acid powder represented by the following formula (I), (B) an inorganic powder, and (C) an oil material:

$$RCONH(CH_2)_m CHCOOH \quad\quad (I)$$
$$| $$
$$NH_2$$

wherein R is a saturated or unsaturated straight hydrocarbon group having 5-9 carbon atoms, and m is an integer of 1-4.

7 Claims, No Drawings

COSMETIC COMPOSITION

CROSS REFERENCES TO RELATED APPLICATIONS

This application is a continuation of International Patent Application No. PCT/JP2014/056764, filed on Mar. 13, 2014, and claims priority to Japanese Patent Application No. 2013-051479, filed on Mar. 14, 2013, all of which are incorporated herein by reference in their entireties.

BACKGROUND OF THE INVENTION

Field of the Invention

The present invention relates to a cosmetic composition containing an N-medium-chain-acyl basic amino acid powder, an inorganic powder and an oil material.

Discussion of the Background

N-long-chain-acyl basic amino acid having an acyl group having 11 or more carbon atoms has a particular plate-like crystal structure, which affords good slipperiness, and is used as a powder material for cosmetics. The N-long-chain-acyl basic amino acid powder further has an effect of suppressing gloss and stickiness of cosmetics, which are derived from an oily material therein (patent document 1). In addition, there is a known technique for suppressing a hard feeling during use and a drying feeling, which are characteristic of inorganic powders, and affording a soft feeling of touch and high moisturizing feeling, by using N-long-chain-acyl basic amino acid as a surface treating agent for inorganic powders (patent document 2).

However, as stated in patent document 2, N-long-chain-acyl basic amino acid that exists separately without adhering to a surface of inorganic powder impairs the slipperiness, smoothness and spreadability of a cosmetic obtained using inorganic powder and N-long-chain-acyl basic amino acid, and sometimes also impairs translucency and luminous finish of the skin after application, since the cosmetic fails to form a uniform coated film. This problem becomes more remarkable when an N-long-chain-acyl basic amino acid powder and an oily material are combined. Furthermore, when a solid cosmetic is produced by pressing a composition containing an N-long-chain-acyl basic amino acid powder, the solid cosmetic sometimes becomes too hard. In this case, problems occur in that the "pick up" of the solid cosmetic to a sponge and the like that rub the surface of a solid cosmetic becomes poor, and a phenomenon of "glossy surface" occurs on the surface of a solid cosmetic by continuously rubbing the surface with a sponge and the like. The Examples of the aforementioned patent documents 1 and 2 do not describe a cosmetic containing N-medium-chain-acyl basic amino acid having a medium-chain acyl group having 6-10 carbon atoms.

Also, patent document 3 describes a skin and hair cosmetic composition containing N-long-chain-acyl basic amino acid, and patent document 4 describes a hair cosmetic composition containing N-long-chain-acyl basic amino acid. However, the Examples of patent documents 3 and 4 do not describe a cosmetic containing an N-medium-chain-acyl basic amino acid powder, an inorganic powder and an oil agent.

DOCUMENT LIST

Patent Documents patent document 1: JP-A-8-337519
patent document 2: JP-A-2001-279129
patent document 3: JP-A-61-137808
patent document 4: JP-A-1-242517

SUMMARY OF THE INVENTION

Problems to be Solved by the Invention

The problem to be solved by the present invention is to provide a cosmetic having a soft and non-drying feel, superior in slipperiness, smoothness and spreadability on application, and affording superior translucency and luminous finish of the skin after application, which, after being pressed into a solid cosmetic, is superior in pick up, impact resistance, and less to develop a glossy surface.

Means of Solving the Problems

The present inventors have conducted intensive studies and found that the above-mentioned problem can be solved by combining a particular N-medium-chain-acyl basic amino acid powder, an inorganic powder and an oil material, which resulted in the completion of the present invention.

Accordingly, the present invention includes the following embodiments.

[1] A cosmetic composition comprising
(A) a powder composed of one or more kinds of N-medium-chain-acyl basic amino acid represented by the formula (I):

wherein R is a saturated or unsaturated straight hydrocarbon group having 5-9 carbon atoms, and m is an integer of 1-4,
(B) an inorganic powder, and
(C) an oil material.
[2] The cosmetic composition of the aforementioned [1], wherein component (A) has an internal frictional angle of 10.0-17.0 degrees.
[3] The cosmetic composition of the aforementioned [1], wherein component (A) is a powder composed of $N^\varepsilon$-monooctanoyl lysine.
[4] The cosmetic composition of any of the aforementioned [1] to [3], wherein the content of component (A) is 0.1-95 wt % of the whole cosmetic composition.
[5] The cosmetic composition of any of the aforementioned [1] to [4], wherein the content of component (B) is 4-99.5 wt % of the whole cosmetic composition.
[6] The cosmetic composition of any of the aforementioned [1] to [5], wherein the content of component (C) is 0.01-95 wt % of the whole cosmetic composition.
[7] The cosmetic composition of any of the aforementioned [1] to [6], wherein a mixing ratio of component (A) and component (B) (weight of component (A): weight of component (B)) is 1:99-60:40.
[8] The cosmetic composition of any of the aforementioned [1] to [7], wherein a mixing ratio of component (A) and component (C) (weight of component (A): weight of component (C)) is 0.5:99.5-90:10.
[9] The cosmetic composition of any of the aforementioned [1] to [8], which is a solid cosmetic.

Effect of the Invention

According to the present invention, a cosmetic having a soft and non-drying feel, superior in slipperiness, smoothness and spreadability on application, and affording superior translucency and luminous finish of the skin after application, which, after being pressed into a solid cosmetic, is superior in pick up, impact resistance, and slightly develops a glossy surface can be obtained.

DETAILED DESCRIPTION OF THE PREFERRED EMBODIMENTS

The cosmetic composition of the present invention is characterized in that it contains (A) a powder composed of N-medium-chain-acyl basic amino acid represented by the formula (I) ((sometimes to be abbreviated as "component (A)"), (B) an inorganic powder ((sometimes to be abbreviated as "component (B)"), and (C) an oil material ((sometimes to be abbreviated as "component (C)") in combination. Using a combination of component (A)-(C), the aforementioned effect of the present invention can be achieved. Components (A)-(C) are sequentially explained below.

[(A) N-Medium-Chain-Acyl Basic Amino Acid Powder]

Component (A) is a powder composed of one or more kinds of N-medium-chain-acyl basic amino acid represented by the formula (I):

$$RCONH(CH_2)_m CHCOOH \atop | \atop NH_2 \qquad (I)$$

wherein R is a saturated or unsaturated straight hydrocarbon group having 5-9 carbon atoms, and m is an integer of 1-4.

R is a saturated or unsaturated straight hydrocarbon group having 5-9 carbon atoms. The number of the carbon atoms is preferably 5, 7 or 9, more preferably 5 or 7, further preferably 7. The hydrocarbon group is preferably an alkyl group. Examples of the alkyl group include a pentyl group, a hexyl group, a heptyl group, an octyl group, a nonyl group and the like, preferably a pentyl group, a hexyl group, a nonyl group, more preferably a pentyl group, a heptyl group, further preferably a heptyl group. m is an integer of 1-4, preferably 2-4, more preferably 3 or 4, further preferably 4.

Component (A) is preferably a powder composed of at least one selected from the group consisting of $N^\varepsilon$-monohexanoyl lysine (a compound of the formula (I), wherein R is a pentyl group and m is an integer of 4), $N^\varepsilon$-monooctanoyl lysine (a compound of the formula (I), wherein R is a heptyl group and m is an integer of 4) and $N^\varepsilon$-monodecanoyl lysine (a compound of the formula (I), wherein R is a nonyl group and m is an integer of 4), and is more preferably a powder composed of $N^\varepsilon$-monooctanoyl lysine.

Component (A) can be synthesized by, for example, a known method such as dehydration condensation of fatty acid and basic amino acid. Examples of the fatty acid to be used for the dehydration condensation include n-hexanoic acid, n-heptanoic acid, n-octanoic acid, n-nonanoic acid, and n-decanoic acid. Examples of the basic amino acid include 2,3-diaminopropionic acid, α,γ-diaminobutyric acid, ornithine and lysine. Only one kind of fatty acid and basic amino acid may be used or a mixture of two or more kinds thereof may be used.

The basic amino acid to be used for the dehydration condensation may be a free form or a salt. Examples of the basic amino acid salt include hydrochloride, acetate, sulfate, carbonate and the like. As the basic amino acid to be used for the dehydration condensation, a free form, hydrochloride and carbonate are preferable, and a free form and carbonate are more preferable. For the dehydration condensation, a mixture of a free form and a salt of the basic amino acid, or a mixture of two or more kinds of basic amino acid salts can also be used.

The reaction temperature of the dehydration condensation is preferably 70° C. to 250° C., more preferably 70° C. to 200° C. to prevent a side reaction, and further preferably 75° C. to 180° C.

Examples of the solvent for the dehydration condensation include toluene, xylene, hexane, heptane, octane, nonane, decane, undecane, dodecane, tridecane, tetradecane, pentadecane, hexadecane, heptadecane, octadecane, cyclohexane, N,N-dimethylformamide, N,N-dimethyl sulfoxide, N-methylpyrrolidone, propanol, butanol, hexanol, heptanol, octanol, acetic acid, acetonitrile and the like. One kind of the solvent may be used or two or more kinds of the solvents may be used in combination. To prevent a side reaction, toluene, xylene, hexane, heptane, octane, nonane, decane, undecane, dodecane, tridecane, tetradecane, pentadecane, hexadecane, heptadecane, octadecane, cyclohexane, N,N-dimethylformamide, N,N-dimethyl sulfoxide and N-methylpyrrolidone are preferable, and toluene, xylene, decane, undecane, dodecane, tridecane, tetradecane, pentadecane, hexadecane, heptadecane, octadecane and cyclohexane are more preferable. In addition, in view of the reaction facility, a solvent having a higher boiling point than the reaction temperature to be employed is preferable.

Component (A) (i.e., N-medium-chain-acyl basic amino acid powder) has an internal frictional angle of preferably 10.0-17.0 degrees, more preferably 11.0-16.0 degrees, further preferably 11.5-16.0 degrees, particularly preferably 12.0-15.0 degrees. The internal frictional angle is a value that varies depending on the kinds of the basic amino acid moiety and acyl group of the N-medium-chain-acyl basic amino acid powder, the amount of fine particles contained in the powder, the conversion degree (particularly, residual ratio of starting material fatty acid) during production of the powder, and the like. The internal frictional angle can be adjusted to fall within the aforementioned preferable range by, for example, selecting the basic amino acid moiety and acyl group in the formula (I), reducing the amount of fine particles having a particle size of 5 μm or below, and setting the conversion degree to not less than 97% (particularly, setting the residual ratio of the starting material fatty acid to not more than 0.5 wt %). It is also possible to obtain a powder having a preferable internal frictional angle by appropriately mixing two or more kinds of N-medium-chain-acyl basic amino acid powders having different internal frictional angles.

The internal frictional angle of component (A) (i.e., N-medium-chain-acyl basic amino acid powder) is determined by a constant pressure shear measurement using a powder bed shear stress analyzer manufactured by Nano Seeds Corporation, and mainly utilized, as a property value showing the flowability of a powder bed, for the facility designs for the production and transportation. The measurement can be performed based on the property evaluation of a finely divided powder for preparation formulation, by using, for example, the powder bed shear stress analyzer NS-S series (e.g., NS-S500) described in the Journal of Japan Society of Pharmaceutical Machinery and Engineering 68 (Vol. 19 No. 1), 2010, 62-67, and the contents of this reference are incorporated in full herein. To be specific, an N-medium-chain-acyl basic amino acid powder (2.5 g) is filled in a shear cell, the top surface of the powder bed is flattened, and a shear test is performed with a target indentation load as a condition for controlling the indentation. When the target load (five stages of 25, 50, 75, 100, 125N) is achieved, indentation is stopped, sideslip is started, and continuous shear stress is recorded on the shear plane. The maximum shear stress of the powder bed is plotted on the vertical axis and the base normal stress of the powder bed at the time point when the maximum shear stress is achieved, is plotted on the horizontal axis, the linear regression equation is calculated, and the angle is determined as an internal frictional angle.

The average particle size of component (A) (i.e., N-medium-chain-acyl basic amino acid powder) of the present invention is preferably 1-1000 μm, more preferably 5-200 μm. The average particle size is determined by measuring the particle size distribution of the N-medium-chain-acyl basic amino acid powder by a laser diffraction/scattering particle size distribution analyzer.

While the content of component (A) in the cosmetic composition of the present invention varies depending on the coexisting components, it is preferably 0.1-95 wt % of the whole cosmetic composition. The lower limit of the content is more preferably 0.5 wt %, still more preferably 1.0 wt %, further preferably 2 wt %, still further preferably 5 wt %. For the feeling of the composition, the upper limit of the content is more preferably 85 wt %, still more preferably 65 wt %, further preferably 55 wt %, still further preferably 45 wt %, particularly preferably 35 wt %.

The cosmetic composition of the present invention is preferably substantially free of an N-long-chain-acyl basic amino acid acyl group having 11 or more carbon atoms. The N-long-chain-acyl basic amino acid tends to impair the effect of the invention afforded by combining component (A) (i.e., N-medium-chain-acyl basic amino acid powder) with components (B) and (C): slipperiness, smoothness and spreadability of a cosmetic, and translucency and luminous finish of the skin after application of a cosmetic. As used herein, being substantially free of N-long-chain-acyl basic amino acid means that the amount of N-long-chain-acyl basic amino acid in the total of component (A) and N-long-chain-acyl basic amino acid in the cosmetic composition of the present invention is less than 10 mol %. The amount of N-long-chain-acyl basic amino acid is more preferably less than 5 mol %, still more preferably less than 1 mol %, further preferably less than 0.1 mol %, of the total of component (A) and N-long-chain-acyl basic amino acid.

[(B) Inorganic Powder]

Examples of the inorganic powder to be used in the cosmetic composition of the present invention include yellow iron oxide, red iron oxide, black iron oxide, fine particles of iron oxide, bismuth oxychloride, zirconium oxide, magnesium oxide, chrome oxide, cobalt oxide, carbon black, ultramarine blue, iron blue, zinc oxide, fine particles of zinc oxide, titanium dioxide, fine particles of titanium dioxide, silica, porous silica, alumina, cerium oxide, boron nitride, calcium sulfate, barium sulfate, magnesium sulfate, calcium carbonate, magnesium carbonate, aluminum silicate, magnesium silicate, silicon carbide, dye, lake, sericite, mica, talc, kaolin, clay, bentonite, plate-like barium sulfate, butterfly-like barium sulfate, hydroxyapatite and the like. One kind of these may be used or two more kinds thereof may be used in combination. Furthermore, the inorganic powder may be a complex of those mentioned above (e.g., silica-coated titanium dioxide, mica-coated titanium dioxide, titanium-coated mica), and may be those mentioned above which are subjected to a surface treatment such as a silicone treatment, a fluorine compound treatment, a silane coupling agent treatment, a silane treatment, an organic titanate treatment, a fatty acid treatment (e.g., stearoylglutamic acid treatment), a metal soap treatment (e.g., aluminum stearate treatment), an oil material treatment, an amino acid treatment and the like (e.g., silicone-treated talc, silicone-treated mica, silicone-treated sericite, silicone-treated titanium dioxide, silicone-treated red iron oxide, silicone-treated yellow iron oxide, silicone-treated black iron oxide, stearoylglutamic acid-treated titanium dioxide, stearoylglutamic acid-treated yellow iron oxide, stearoylglutamic acid-treated red iron oxide, stearoylglutamic acid-treated black iron oxide, aluminum stearate-treated titanium dioxide and the like).

In the cosmetic composition of the present invention containing talc as component (B), the effect of the present invention appears more remarkably. Therefore, talc is preferably used as component (B).

While the content of component (B) in the cosmetic composition of the present invention varies depending on the coexisting component, it is preferably 4-99.5 wt % of the whole cosmetic composition. The lower limit of the content is more preferably 5 wt %, still more preferably 10 wt %, further preferably 20 wt %, still further preferably 30 wt %. For the feeling of the composition, the upper limit of the content is more preferably 95 wt %, still more preferably 93 wt %, further preferably 90 wt %.

[(C) Oil Material]

The oil material to be used in the cosmetic composition the present invention is not particularly limited as long as it is generally used for cosmetics. Examples thereof include solid or paste oil such as petrolatum, lanolin, ceresin, microcrystalline wax, carnauba wax, candelilla wax, shea butter and the like; higher fatty acid such as stearic acid, isostearic acid and the like; higher alcohol such as cetanol, stearyl alcohol, behenyl alcohol, octyldodecanol, oleyl alcohol and the like; hydrocarbon oil such as squalane, liquid paraffin, hydrogenated polyisobutene, isododecane and the like; natural or synthetic ester oil such as jojoba seed oil, isononyl isononanoate, isostearyl neopentanoate, cetyl 2-ethylhexanoate, ethylhexyl palmitate, alkyl benzoate, polyglyceryl-2 tetraisostearate, phytosteryl/octyldodecyl lauroyl glutamate, isopropyl lauroyl sarcosinate, phytosteryl/octyldodecyl/behenyl lauroyl glutamate, ethylhexyl methoxycinnamate, phytosteryl/decyltetradecyl myristoyl methyl beta-alanininate, glyceryl caprate and the like; diglycerides; natural or synthetic triglyceride such as corn oil, olive oil, sunflower oil, caprylic/capric triglyceride, triethylhexanoin and the like; high viscous oil such as phytosteryl/isostearyl/cetyl/stearyl/behenyl dimer dilinoleate, diisostearyl malate, hydrogenated polydecene, polyglyceryl-2 triisostearate, polyglyceryl-2 diisostearate, pentaerythrityl tetraisostearate and the like; silicone oil such as dimethicone, methicone, cyclopentasiloxane, cyclohexasiloxane, phenyl trimethicone, PEG-10 dimethicone and the like; fluorinated oil material such as perfluoropolyether, perfluorodecalin, perfluorooctane and the like; mineral oil; and the like. One kind of thereof may be used or two more kinds thereof may be used in combination.

The content of component (C) in the cosmetic composition of the present invention varies depending on the coexisting components, and it is preferably 0.01-95 wt % of the whole cosmetic composition. The lower limit of the content is more preferably 0.05 wt %, still more preferably 0.1 wt %, further preferably 0.5 wt %, still further preferably 1.0 wt %. The upper limit of the content is more preferably 93 wt %, still more preferably 90 wt %, further preferably 85 wt %, still further preferably 70 wt %, particularly preferably 50 wt %.

The cosmetic composition of the present invention preferably contains 0.1-95 wt % of component (A), 4-99.5 wt % of component (B) and 0.01-95 wt % of component (C); more preferably 0.5-85 wt % of component (A), 5-95 wt % of component (B) and 0.05-93 wt % of component (C); still more preferably 1.0-65 wt % of component (A), 10-93 wt % of component (B) and 0.1-90 wt % of component (C); further preferably 2-55 wt % of component (A), 20-90 wt % of component (B) and 0.5-85 wt % of component (C); still further preferably 5-45 wt % of component (A), 30-90 wt % of component (B) and 1.0-70 wt % of component (C); particularly preferably 5-35 wt % of component (A), 30-90 wt % of component (B) and 1.0-50 wt % of component (C). The aforementioned contents are the values relative to the whole cosmetic composition.

The mixing ratio of component (A) and component (B) in the cosmetic composition of the present invention (weight of component (A): weight of component (B)) is preferably 1:99-60:40, more preferably 1.5:98.5-40:60, still more preferably 2:98-35:65, further preferably 5:95-32:68.

The mixing ratio of component (A) and component (C) in the cosmetic composition of the present invention (weight of component (A): weight of component (C)) is preferably 0.5:99.5-90:10, more preferably 1:99-85:15, still more preferably 10:90-80:20, further preferably 15:85-75:25, still further preferably 30:70-72:28.

The cosmetic composition of the present invention can be used for various uses aiming at controlling and/or adding the color of the skin or lips, and/or UV shielding. The cosmetic composition of the present invention may be a solid cosmetic or a liquid cosmetic, preferably a solid cosmetic. Examples of the solid cosmetics include loose powder type cosmetics; solid powder cosmetics formed by filling a container, followed by compression molding, or removal of solvent; paste cosmetics formed by feeding the paste in a container; stick type cosmetics; and the like. Examples of the liquid cosmetics include emulsion type cosmetics containing a liquid component (water etc.) and the like. Examples of the use of the cosmetic composition of the present invention include foundation, stick foundation, face powder, lipstick, cheek rouge, eye color, eyebrow, face primer, day serum, sunscreen, concealer, bronzer, lip color, BB cream and the like. The characteristics of the cosmetic composition of the present invention are particularly useful when a comparatively large amount of an inorganic powder is incorporated. Examples of the cosmetics to be used for such use include solid powder cosmetics such as solid powder foundation and the like, powder cosmetics such as loose powder foundation, face powder and the like, various sunscreens, concealers, face primer and the like.

The cosmetic composition of the present invention may contain, besides the above-mentioned components (A)-(C), other components generally usable for cosmetics (including medicinal external preparations and quasi-drugs) as long as the effect of the present invention is not inhibited. Examples of other components include water, surfactant, amino acid, amino acid derivative, lower alcohol (e.g., ethanol), polyvalent alcohol (e.g., glycerin, butyleneglycol), sugar alcohol and alkylene oxide adduct thereof, water-soluble polymer (e.g., hydroxyethyl cellulose), film-forming polymer, resin powder (e.g., nylon powder, (dimethicone/vinyldimethicone) crosspolymer powder), clay mineral (e.g., quaternium-18 hectorite, quaternium-18 bentonite), gelling agent (e.g., dibutyl lauroyl glutamide, dibutyl ethylhexanoyl glutamide), moisturizing agent (e.g., sodium pyrrolidone carboxylate), bactericide and antibacterial agent, anti-inflammatory agent, analgesic, antifungal agent, an agent for softening or peeling corneum, skin colorant, hormone preparation, UV absorber, hair growing agent, antiperspirant and astringent active ingredient (e.g., zinc pyrrolidone carboxylate salt), perspiration deodorant, vitamin, blood flow promoter (vasodilator, blood circulation promoter), crude drug, plant extract, pH adjuster, chelating agent (e.g., EDTA-2Na), viscosity modifier, pearlescent agent, natural fragrance, synthetic fragrance, dye and pigment (e.g., Red No. 202, Blue No. 1), antioxidant (e.g., tocopherol, tocopherol acetate, glucosyl pentagallate), preservative (e.g., methylparaben, butylparaben, propylparaben, phenoxyethanol), emulsifier, thickener, fat and wax, silicone compound, balm and the like.

The cosmetic composition of the present invention can be produced by mixing components (A)-(B) and, as necessary, other components by a known method. For example, the cosmetic composition of the present invention can be produced by adding component (C) and, as necessary, other components to powder components (A) and (B), mixing them by a Henschel mixer and the like, and sieving the obtained mixture. The cosmetic composition of the present invention can also be produced by coating a partial or whole amount of component (B) with a partial or whole amount of component (A) by a known method, and mixing component (B) coated with component (A) and the rest of component (A) (when partly used for coating), the rest of component (B) (when partly used for coating) and component (C) and, as necessary, other components. Examples of the method of coating component (B) with component (A) include a dry processing method utilizing an impact mixer, a shear mixer and the like, and a wet processing method including dropwise addition of a strong alkali solution of component (A) to slurry of component (B), neutralizing same with acid, filtering and drying same. When component (B) is coated with component (A), the amount of component (A) used for coating is not more than 20 parts by weight per 100 parts by weight of component (B) to be coated is desirable.

EXAMPLES

The present invention is explained in more detail in the following by referring to Examples, which are not to be construed as limitative.

[Production Example 1] N-Medium-Chain Acyl Basic Amino Acid Powder having Internal Frictional Angle of 12.9 Degrees n-Octanoic acid (manufactured by Tokyo Chemical Industry Co., Ltd., 93.0 g) and lysine (manufactured by Tokyo Chemical Industry Co., Ltd., 84.5 g) were suspended in xylene (manufactured by KANTO CHEMICAL CO., INC., 439.2 g) at 25° C., and the obtained suspension was heated to 80° C., and stirred at 80° C. for 1 hr to form a lysine salt of n-octanoate. The suspension was further heated, reacted with boiling by heating under a nitrogen atmosphere while removing water produced by the reaction to the outside of the system, and continuously stirred for 3 hr. After cooling, the precipitated crystals were collected by filtration, the crystals obtained were washed with a 50 wt % aqueous ethanol solution (516.0 g) and dried to give $N^{\varepsilon}$-monooctanoyl-L-lysine (white powder, 139.5 g, yield 89.0%) as a powder of Production Example 1.

$^1$H-NMR measurement results of the powder of Production Example 1 (400 MHz, $CD_3COOD$): 4.09 (t, J=11 Hz, 1H, CHCOOH), 3.28 (t, J=13 Hz, 2H, $CH_2NHCO$), 2.29 (t, J=16 Hz, 2H, $CH_2CONH$), 2.04-1.91 (m, 2H, $CH_2CHNH_2$), 1.65-1.46 (m, 6H, CH$_2$CH$_2$CHNH$_2$, CH$_2$CH$_2$NHCO, CH$_2$CH$_2$CONH), 1.36-1.24 (m, 8H, CH$_2$), 0.91 (t, J=14 Hz, 3H, CH$_3$)

Using the powder bed shear stress analyzer NS-S500 manufactured by Nano Seeds Corporation, the powder of Production Example 1 was subjected to a constant pressure shear measurement. The maximum shear stress of 2.5 g of the powder bed was plotted on the vertical axis and the base normal stress of the powder bed at the time point when the maximum shear stress was achieved, was plotted on the horizontal axis, the linear regression equation was calculated, and an internal frictional angle was determined. As a result, the internal frictional angle of the powder of Production Example 1 was 12.9 degrees.

Using the laser diffraction/scattering particle size, distribution analyzer LA-920 manufactured by Horiba, Ltd., the particle size distribution of the powder of Production Example 1 was measured, and the average particle size thereof was determined. As a result, the average particle size of the powder of Production Example 1 was 35 μm.

[Production Example 2] N-Medium-Chain Acyl Basic Amino Acid Powder having Internal Frictional Angle of 15.7 Degrees In the same manner as in Production Example 1 except that n-decanoic acid (manufactured by Tokyo Chemical Industry Co., Ltd., 111.1 g) was used instead of n-octanoic acid (93.0 g), N$^\varepsilon$-monodecanoyl-L-lysine (white powder, 160.7 g, yield 85.0%) was obtained as a powder of Production Example 2.

$^1$H-NMR measurement results of the powder of Production Example 2 (400 MHz, CD$_3$COOD): 4.11 (t, J=11 Hz, 1H, CHCOOH), 3.28 (t, J=13 Hz, 2H, CH2NHCO), 2.27 (t, J=16 Hz, 2H, CH$_2$CONH), 2.06-1.93 (m, 2H, CH$_2$CHNH$_2$), 1.68-1.49 (m, 6H, CH$_2$CH$_2$CHNH$_2$, CH$_2$CH$_2$NHCO, CH$_2$CH$_2$CONH), 1.37-1.29 (m, 12H, CH$_2$) 0.90 (t, J=13 Hz, 3H, CH$_3$)

The internal frictional angle of the powder of Production Example 2 measured in the same manner as in Production Example 1 was 15.7 degrees. In addition, the average particle size of the powder of Production Example 2 measured in the same manner as in Production Example 1 was 14.8 μm.

[Production Example 3] N-Medium-Chain Acyl Basic Amino Acid Powder having Internal Frictional Angle of 11.5 Degrees In the same manner as in Production Example 1 except that n-hexanoic acid (manufactured by Tokyo Chemical Industry Co., Ltd., 74.9 g) was used instead of n-octanoic acid (93.0 g), N$^\varepsilon$-monohexanoyl-L-lysine (white powder, 80.8 g, yield 64.9%) was obtained as a powder of Production Example 3.

$^1$H-NMR measurement results of the powder of Production Example 3 (400 MHz, CD$_3$COOD): 4.09 (t, J=11 Hz, 1H, CHCOOH), 3.28 (t, J=13 Hz, 2H, CH$_2$NHCO), 2.28 (t, J=14 Hz, 2H, CH$_2$CONH), 2.04-1.93 (m, 2H, CH$_2$CHNH$_2$), 1.68-1.48 (m, 6H, CH$_2$CH$_2$CHNH$_2$, CH$_2$CH$_2$NHCO, CH$_2$CH$_2$CONH), 1.38-1.27 (m, 4H, CH$_2$), 0.92 (t, J=13 Hz, 3H, CH$_3$)

The internal frictional angle of the powder of Production Example 3 measured in the same manner as in Production Example 1 was 11.5 degrees. In addition, the average particle size of the powder of Production Example 3 measured in the same manner as in Production Example 1 was 55 μm.

[Production Example 4] N-Medium-Chain Acyl Basic Amino Acid Powder having Internal Frictional Angle of 12.1 Degrees The powder of Production Example 1 (4 g), the powder of Production Example 2 (8 g) and the powder of Production Example 3 (4 g) were placed in a small container for a laboratory grinding machine (trade name Millser LFM-800DG, manufactured by Iwatani Corporation) and mixed for 5 min to give a powder of Production Example 4 as a white powder.

The internal frictional angle of the powder of Production Example 4 measured in the same manner as in Production Example 1 was 12.1 degrees. In addition, the average particle size of the powder of Production Example 4 measured in the same manner as in Production Example 1 was 30 μm.

[Comparative Example 1] N-Long-Chain-Acyl Basic Amino Acid Powder having Internal Frictional Angle of 17.7 Degrees As a powder of Comparative Example 1, "Amihope LL" manufactured by Ajinomoto Co., Inc. (N$^\varepsilon$-monododecanoyl-L-lysine) was used. The internal frictional angle of the powder of Comparative Example 1 measured in the same manner as in Production Example 1 was 17.7 degrees. In addition, the average particle size of the powder of Comparative Example 1 measured in the same manner as in Production Example 1 was 23.5 μm.

[Examples 1-8][Comparative Examples 2-4] Solid Powder Cosmetic Composition

Solid powder foundations (solid powder cosmetic composition) having the compositions (unit: wt %) shown in Table 1-1 to Table 1-4 were produced, and pick up, slipperiness, translucency, luminous finish, smoothness, spreadability, adhesiveness, glossy surface, impact resistance, softness on application and non-drying feel after application were evaluated. The results are shown in Table 1-1 to Table 1-5.

[Production of Solid Powder Foundation]

An oil material was added to the N-medium-chain-acyl basic amino acid powder of Production Example 1-4 or N-long chain N-acyl basic amino acid powder of Comparative Example 1 and an inorganic powder, they were mixed by a Henschel mixer, and the obtained mixture was filtered through a 250 μm mesh sieve. The mixture (about 12 g) was filled in an aluminum middle plate, and press-molded at 0.4 MPa to give a solid powder foundation.

<Evaluation of Pick Up>

The surface of a solid powder foundation was rubbed once with a commercially available foundation sponge, the amount of the foundation left on the sponge was visually evaluated, and pick up was evaluated according to the following criteria.

⊙ much foundation is picked up in one time
○ sufficient amount of foundation is picked up in one time
Δ small amount is picked up in one time
× extremely small amount is picked up in one time <Evaluations of Slipperiness, Translucency and Luminous Finish>

Black artificial leather manufactured by Idemitsu Technofine Co., Ltd. (trade name SUPPLALE) was adhered to a microscope slide glass, and 4 of which were prepared for each Example and Comparative Example. The solid powder foundation was spread once in the long axis direction of the aforementioned artificial leather with a commercially available foundation sponge, and the slipperiness during spreading, and translucency and luminous finish of the obtained coating film were evaluated according to the following criteria.

⊙ extremely good
○ good
Δ rather bad
× bad

<Evaluation of Smoothness>

The coating films obtained in the above-mentioned evaluation test for slipperiness, translucency and luminous finish were observed visually or under a fiber microscope (X200) for uneven coating film and coagulation of powder, and the smoothness was evaluated according to the following criteria.

⊙ almost no uneven coating by visual observation and fiber microscopic observation, and uniform coating film is obtained
○ less uneven coating by visual observation, but coagulation of powder by fiber microscopic observation
Δ rather notable uneven coating by visual observation, and many coagulations of powder by fiber microscopic observation
× remarkable coagulation and uneven coating by visual observation <Evaluation of Spreadability>

The coating films obtained in the above-mentioned evaluation tests for slipperiness, translucency and luminous finish were photographed with a fiber microscope (×200). From the obtained images, the proportion of the area of the bright part having a brightness level of not less than 100 relative to the total photographed area (=100× area of bright part having brightness level of not less than 100/total photographed area) was calculated. This was repeated 4 times, and an average of the obtained four calculations of the 4 images was taken as a cover ratio of the solid powder foundation. The spreadability was evaluated from the obtained cover ratios according to the following criteria.

⊙ cover ratio not less than 95%
○ cover ratio not less than 85% and less than 95%
Δ cover ratio not less than 75% and less than 85%
× cover ratio less than 75%

<Evaluation of Adhesiveness>

An adhesive tape (Cellotape manufactured by Nichiban Co., Ltd.) is placed on the coating film obtained in the above-mentioned evaluation test for the slipperiness, translucency and luminous finish, adhered by lightly pressing with the ball of a finger, and the adhesive tape was detached. The coating film on the artificial leather after detachment was photographed by a fiber microscope (×200) again and the cover ratio after detachment was determined from the obtained image in the same manner as in the spreadability evaluation test. The residual ratio (=100× cover ratio after detachment/cover ratio) was determined from the cover ratio obtained by the spreadability evaluation test and the cover ratio after detachment obtained by this test, and the adhesiveness was evaluated according to the following criteria.

⊙ residual ratio not less than 95%
○ residual ratio not less than 85% and less than 95%
Δ residual ratio not less than 75% and less than 85%
× residual ratio less than 75%

<Evaluation of Glossy Surface>

The same part of the surface of a solid powder foundation was strongly rubbed with a commercially available foundation sponge, the number of rubbings necessary for obtaining a glossy surface was counted, and the glossy surface was evaluated according to the following criteria.

⊙ no glossy surface after rubbing by 20 reciprocations
○ glossy surface after rubbing by 11-20 reciprocations
Δ glossy surface after rubbing by 6-10 reciprocations
× glossy surface after rubbing by 5 reciprocations or below <Impact Resistance>

A solid powder foundation was repeatedly dropped from a 50 cm height onto a floor covered with a vinyl cloth, the number of droppings necessary for producing damage such as chipping, cracking and the like was counted, and the impact resistance was evaluated according to the following criteria.

⊙ no damage by dropping 20 times
○ damage by dropping 11-20 times
Δ damage by dropping 6-10 times
× damage by dropping 5 times or below <Evaluation of Softness on Application, and Non-Drying Feel after Application>

The solid powder foundation was applied to the inside of lower arm with a commercially available foundation sponge and the feeling of use at that time was graded by five panelists according to the following criteria. An average score was obtained, and the softness on application and non-drying feel after application were evaluated according to the following criteria.

(Grading Criteria of Softness on Application)
4 very high softness on application
3 high softness on application
2 normal softness on application
1 less softness on application
0 no softness on application (Grading Criteria of Non-Drying Feel after Application)
4 very high non-drying feel after application
3 high non-drying feel after application
2 normal non-drying feel after application
1 less non-drying feel after application
0 no non-drying feel after application (Evaluation Criteria)
⊙ average score not less than 3.0
○ average score not less than 2.0 and less than 3.0
Δ average score not less than 2.0 and less than 2.0
× average score less than 1.0

TABLE 1-1

|  |  | Ex. 1 | Ex. 2 |
|---|---|---|---|
| component (A) | powder of Production Ex. 1 | 2.00 | 5.00 |
|  | powder of Production Ex. 2 | — | — |
|  | powder of Production Ex. 3 | — | — |
|  | powder of Production Ex. 4 | — | — |
|  | powder of Com. Ex. 1 | — | — |
| component (B) | silicone-treated talc | 22.00 | 21.00 |
|  | silicone-treated mica | 31.00 | 30.00 |
|  | silicone-treated sericite | 19.40 | 18.40 |
|  | silicone-treated titanium dioxide | 8.00 | 8.00 |
|  | titanium dioxide | 3.00 | 3.00 |
|  | zinc oxide | 2.00 | 2.00 |
|  | silicone-treated red iron oxide | 0.40 | 0.40 |
|  | silicone-treated yellow iron oxide | 1.05 | 1.05 |

TABLE 1-1-continued

|  |  | Ex. 1 | Ex. 2 |
|---|---|---|---|
|  | silicone-treated black iron oxide | 0.15 | 0.15 |
| component (C) | dimethicone | 5.00 | 5.00 |
|  | polyglyceryl-2 tetraisostearate | 3.00 | 3.00 |
|  | phytosteryl/decyltetradecyl myristoyl methyl beta-alaninate | 1.00 | 1.00 |
|  | mineral oil | 2.00 | 2.00 |
|  | total (wt %) | 100.00 | 100.00 |
|  | component (A) content (wt %) | 2.00 | 5.00 |
|  | component (B) content (wt %) | 87.00 | 84.00 |
|  | component (C) content (wt %) | 11.00 | 11.00 |
|  | component (A) weight: component (B) weight | 2.2:97.8 | 5.6:94.4 |
|  | component (A) weight: component (C) weight | 15.4:84.6 | 31.3:68.8 |
| evaluation | pick up | ◉ | ◉ |
|  | slipperiness | ○ | ◉ |
|  | translucency | ◉ | ◉ |
|  | luminous finish | ○ | ◉ |
|  | smoothness | ○ | ◉ |
|  | spreadability | ◉ | ◉ |
|  | adhesiveness | ◉ | ◉ |
|  | glossy surface | ◉ | ◉ |
|  | impact resistance | ○ | ◉ |

TABLE 1-2

|  |  | Ex. 3 | Ex. 4 | Ex. 5 |
|---|---|---|---|---|
| component (A) | powder of Production Ex. 1 | 12.40 | 27.4 | 32.40 |
|  | powder of Production Ex. 2 | — | — | — |
|  | powder of Production Ex. 3 | — | — | — |
|  | powder of Production Ex. 4 | — | — | — |
|  | powder of Com. Ex. 1 | — | — | — |
| component (B) | silicone-treated talc | 18.00 | 14.00 | 13.00 |
|  | silicone-treated mica | 27.00 | 20.00 | 18.00 |
|  | silicone-treated sericite | 17.00 | 13.00 | 11.00 |
|  | silicone-treated titanium dioxide | 8.00 | 8.00 | 8.00 |
|  | titanium dioxide | 3.00 | 3.00 | 3.00 |
|  | zinc oxide | 2.00 | 2.00 | 2.00 |
|  | silicone-treated red iron oxide | 0.40 | 0.40 | 0.40 |
|  | silicone-treated yellow iron oxide | 1.05 | 1.05 | 1.05 |
|  | silicone-treated black iron oxide | 0.15 | 0.15 | 0.15 |
| component (C) | dimethicone | 5.00 | 5.00 | 5.00 |
|  | polyglyceryl-2 tetraisostearate | 3.00 | 3.00 | 3.00 |
|  | phytosteryl/decyltetradecyl myristoyl methyl beta-alaninate | 1.00 | 1.00 | 1.00 |
|  | mineral oil | 2.00 | 2.00 | 2.00 |
|  | total (wt %) | 100.00 | 100.00 | 100.00 |
|  | component (A) content (wt %) | 12.40 | 27.4 | 32.40 |
|  | component (B) content (wt %) | 76.60 | 50.6 | 56.60 |
|  | component (C) content (wt %) | 11.00 | 11.00 | 11.00 |
|  | component (A) weight: component (B) weight | 13.9:86.1 | 35.1:64.9 | 36.4:63.6 |
|  | component (A) weight: component (C) weight | 53:47 | 71.4:28.6 | 74.7:25.3 |
| evaluation | pick up | ◉ | ◉ | ○ |
|  | slipperiness | ○ | ◉ | ◉ |
|  | translucency | ◉ | ◉ | ◉ |
|  | luminous finish | ◉ | ◉ | ◉ |
|  | smoothness | ◉ | ◉ | ◉ |
|  | spreadability | ◉ | ◉ | ○ |
|  | adhesiveness | ◉ | ◉ | ◉ |
|  | glossy surface | ◉ | ○ | ○ |
|  | impact resistance | ◉ | ◉ | ◉ |

TABLE 1-3

|  |  | Ex. 6 | Ex. 7 | Ex. 8 |
|---|---|---|---|---|
| component (A) | powder of Production Ex. 1 | — | — | — |
|  | powder of Production Ex. 2 | 32.40 | — | — |
|  | powder of Production Ex. 3 | — | 32.40 | — |
|  | powder of Production Ex. 4 | — | — | 5.00 |
|  | powder of Com. Ex. 1 | — | — | — |
| component (B) | silicone-treated talc | 13.00 | 13.00 | 21.00 |
|  | silicone-treated mica | 18.00 | 18.00 | 30.00 |
|  | silicone-treated sericite | 11.00 | 11.00 | 18.40 |
|  | silicone-treated titanium dioxide | 8.00 | 8.00 | 8.00 |
|  | titanium dioxide | 3.00 | 3.00 | 3.00 |
|  | zinc oxide | 2.00 | 2.00 | 2.00 |
|  | silicone-treated red iron oxide | 0.40 | 0.40 | 0.40 |
|  | silicone-treated yellow iron oxide | 1.05 | 1.05 | 1.05 |
|  | silicone-treated black iron oxide | 0.15 | 0.15 | 0.15 |
| component (C) | dimethicone | 5.00 | 5.00 | 5.00 |
|  | polyglyceryl-2 tetraisostearate | 3.00 | 3.00 | 3.00 |
|  | phytosteryl/decyltetradecyl myristoyl methyl beta-alaninate | 1.00 | 1.00 | 1.00 |
|  | mineral oil | 2.00 | 2.00 | 2.00 |
|  | total (wt %) | 100.00 | 100.00 | 100.00 |
|  | component (A) content (wt %) | 32.40 | 32.40 | 5.00 |
|  | component (B) content (wt %) | 56.60 | 56.60 | 84.00 |
|  | component (C) content (wt %) | 11.00 | 11.00 | 11.00 |
|  | component (A) weight: component (B) weight | 36.4:63.6 | 36.4:63.6 | 5.6:94.4 |
|  | component (A) weight: component (C) weight | 74.7:25.3 | 74.7:25.3 | 31.3:68.8 |
| evaluation | pick up | ○ | ○ | ◉ |
|  | slipperiness | ◉ | ◉ | ◉ |
|  | translucency | ◉ | ◉ | ○ |
|  | luminous finish | ○ | ◉ | ◉ |
|  | smoothness | ◉ | ◉ | ◉ |
|  | spreadability | ○ | ○ | ◉ |
|  | adhesiveness | ◉ | ○ | ◉ |
|  | glossy surface | ○ | ○ | ◉ |
|  | impact resistance | ◉ | ◉ | ◉ |

TABLE 1-4

|  |  | Com. Ex. 2 | Com. Ex. 3 | Com. Ex. 4 |
|---|---|---|---|---|
| component (A) | powder of Production Ex. 1 | — | — | — |
|  | powder of Production Ex. 2 | — | — | — |
|  | powder of Production Ex. 3 | — | — | — |
|  | powder of Production Ex. 4 | — | — | — |
|  | powder of Com. Ex. 1 | — | 12.40 | 32.40 |
| component (B) | silicone-treated talc | 22.40 | 18.00 | 13.00 |
|  | silicone-treated mica | 32.00 | 27.00 | 18.00 |
|  | silicone-treated sericite | 20.00 | 17.00 | 11.00 |
|  | silicone-treated titanium dioxide | 8.00 | 8.00 | 8.00 |
|  | titanium dioxide | 3.00 | 3.00 | 3.00 |
|  | zinc oxide | 2.00 | 2.00 | 2.00 |
|  | silicone-treated red iron oxide | 0.40 | 0.40 | 0.40 |

TABLE 1-4-continued

|  |  | Com. Ex. 2 | Com. Ex. 3 | Com. Ex. 4 |
|---|---|---|---|---|
| component (C) | silicone-treated yellow iron oxide | 1.05 | 1.05 | 1.05 |
| | silicone-treated black iron oxide | 0.15 | 0.15 | 0.15 |
| | dimethicone | 5.00 | 5.00 | 5.00 |
| | polyglyceryl-2 tetraisostearate | 3.00 | 3.00 | 3.00 |
| | phytosteryl/decyltetradecyl myristoyl methyl beta-alaninate | 1.00 | 1.00 | 1.00 |
| | mineral oil | 2.00 | 2.00 | 2.00 |
| | total (wt %) | 100.00 | 100.00 | 100.00 |
| | component (A) content (wt %) | 0.00 | 12.40 | 32.40 |
| | component (B) content (wt %) | 89.00 | 76.60 | 56.60 |
| | component (C) content (wt %) | 11.00 | 11.00 | 11.00 |
| | component (A) weight: component (B) weight | 0:100 | 13.9:86.1 | 36.4:63.6 |
| | component (A) weight: component (C) weight | 0:100 | 53:47 | 74.7:25.3 |
| evaluation | pick up | ⊙ | ○ | Δ |
| | slipperiness | X | Δ | ⊙ |
| | translucency | X | ○ | ⊙ |
| | luminous finish | Δ | X | X |
| | smoothness | ○ | Δ | X |
| | spreadability | ⊙ | Δ | X |
| | adhesiveness | Δ | ⊙ | ⊙ |
| | glossy surface | ⊙ | Δ | X |
| | impact resistance | Δ | ⊙ | ⊙ |

TABLE 1-5

|  |  | Ex. 1 | Ex. 2 | Ex. 3 | Ex. 4 | Ex. 5 | Com. Ex. 2 | Com. Ex. 3 | Com. Ex. 4 |
|---|---|---|---|---|---|---|---|---|---|
| evaluation | softness on application | ⊙ | ⊙ | ⊙ | ⊙ | ⊙ | X | ○ | Δ |
| | non-drying feel after application | ⊙ | ⊙ | ⊙ | ⊙ | ○ | X | ⊙ | ⊙ |

The solid powder foundations of Examples 1-8 were superior in all of pick up, slipperiness, translucency, luminous finish, smoothness, spreadability, adhesiveness, glossy surface, and impact resistance. The solid powder foundations of Examples 1-5 were also superior in the softness on application and non-drying feel after application. Among these, the solid powder foundations of Examples 2-8 are more preferable, the solid powder foundations of Examples 2-4 and 8 are further preferable, and the solid powder foundation of Example 2 was particularly preferable.

On the other hand, the solid powder foundation of Comparative Example 2 was poor in the slipperiness, translucency, softness on application, and non-drying feel after application, and unsatisfactory in the luminous finish, adhesiveness and impact resistance. The solid powder foundation of Comparative Example 3 was poor in the luminous finish, and unsatisfactory in the slipperiness, smoothness, spreadability and glossy surface. The solid powder foundation of Comparative Example 4 was poor in the luminous finish, smoothness, spreadability, and glossy surface, and unsatisfactory in the pick up and softness on application.

The cosmetics of the present invention in other embodiments are shown in Tables 2-7. In Tables 2-7, the unit of the values is wt %.

TABLE 2

| solid powder foundation | |
|---|---|
| silicone-treated talc | 27.8 |
| silicone-treated mica | 12.0 |
| silicone-treated sericite | 12.0 |
| titanium dioxide | 18.5 |
| powder of Production Ex. 1 | 12.6 |
| nylon powder | 2.8 |
| silicone-treated red iron oxide | 0.9 |
| silicone-treated yellow iron oxide | 2.8 |
| silicone-treated black iron oxide | 0.4 |
| petrolatum | 2.0 |
| isononyl isononanoate | 3.0 |
| mineral oil | 2.0 |
| cyclomethicone | 3.0 |
| methylparaben | 0.2 |
| total (wt %) | 100.0 |

TABLE 3

| loose powder foundation | |
|---|---|
| silicone-treated talc | 18.00 |
| silicone-treated mica | 36.90 |
| titanium dioxide | 18.00 |
| aluminum stearate-treated titanium dioxide | 3.00 |
| silicone-treated red iron oxide | 0.60 |
| silicone-treated yellow iron oxide | 1.50 |
| silicone-treated black iron oxide | 0.30 |
| porous silica | 0.50 |
| powder of Production Ex. 1 | 20.00 |
| methylparaben | 0.20 |

TABLE 3-continued

| loose powder foundation | |
|---|---|
| triethylhexanoin | 0.59 |
| phytosteryl/octyldodecyl lauroyl glutamate | 0.20 |
| isopropyl lauroyl sarcosinate | 0.20 |
| tocopherol | 0.01 |
| total (wt %) | 100.0 |

TABLE 4

| stick foundation | |
|---|---|
| octyldodecanol | 20.00 |
| dibutyl lauroyl glutamide | 3.00 |
| dibutyl ethylhexanoyl glutamide | 2.00 |
| triethylhexanoin | 11.00 |
| ethylhexyl methoxycinnamate | 3.00 |
| hydrogenated polyisobutene | 20.00 |
| pentaerythrityl tetraisostearate | 0.50 |
| tocopherol acetate | 0.05 |
| butylparaben | 0.10 |
| propylparaben | 0.10 |
| (dimethicone/vinyldimethicone) crosspolymer powder | 2.00 |

TABLE 4-continued

| stick foundation | |
| --- | --- |
| mica | 1.83 |
| stearoylglutamic acid-treated titanium dioxide | 10.00 |
| silica-coated titanium dioxide | 5.00 |
| cyclopentasiloxane | 11.00 |
| stearoylglutamic acid-treated red iron oxide | 0.42 |
| stearoylglutamic acid-treated yellow iron oxide | 1.41 |
| stearoylglutamic acid-treated black iron oxide | 0.09 |
| quaternium-18 hectorite | 1.00 |
| powder of Production Ex. 1 | 0.50 |
| silica | 7.00 |
| total (wt %) | 100.0 |

TABLE 5

| lipstick | |
| --- | --- |
| ceresin | 10.0 |
| microcrystalline wax | 7.0 |
| diisostearyl malate | 23.8 |
| pentaerythrityl tetraisostearate | 15.0 |
| phytosteryl/octyldodecyl lauroyl glutamate | 10.0 |
| hydrogenated polydecene | 10.0 |
| isostearyl/phytosteryl dimer dilinoleate | 12.0 |
| polyglyceryl-2 triisostearate | 4.5 |
| powder of Production Ex. 1 | 1.0 |
| Red No. 202 | 1.2 |
| Blue No. 1 | 0.3 |
| red iron oxide | 1.2 |
| mica-coated titanium dioxide (white) | 1.0 |
| mica-coated titanium dioxide (red) | 3.0 |
| total (wt %) | 100.0 |

TABLE 6

| BB cream | |
| --- | --- |
| cyclopentasiloxane | 20.00 |
| isononyl isononanoate | 2.00 |
| ethylhexyl methoxycinnamate | 2.50 |
| phytosteryl/octyldodecyl lauroyl glutamate | 0.20 |
| dimethicone | 3.00 |
| polyglyceryl-2 diisostearate | 2.00 |
| PEG-10 dimethicone | 4.30 |
| phenoxyethanol | 0.40 |
| tocopherol acetate | 0.10 |
| quaternium-18 bentonite | 1.30 |
| titanium dioxide | 10.00 |
| powder of Production Ex. 1 | 0.5 |
| silicone-treated red iron oxide | 0.42 |
| silicone-treated yellow iron oxide | 1.41 |
| silicone-treated black iron oxide | 0.09 |
| EDTA-2Na | 0.05 |
| zinc pyrrolidone carboxylate salt | 1.00 |
| glyceryl caprate | 0.30 |
| ethanol | 3.00 |
| glucosyl pentagallate | 0.05 |
| glycerine | 4.00 |
| water | 43.38 |
| total (wt %) | 100.00 |

TABLE 7

| sunscreen | |
| --- | --- |
| cyclomethicone | 25.0 |
| (phytosteryl/octyldodecyl/behenyl)lauroylglutamate | 1.0 |
| tocopherol acetate | 0.1 |
| PEG-10 dimethicone, dimethicone | 2.0 |

TABLE 7-continued

| sunscreen | |
| --- | --- |
| fine particles of titanium dioxide | 5.0 |
| zinc oxide | 10.0 |
| powder of Production Ex. 1 | 3.0 |
| magnesium sulfate | 0.5 |
| sodium pyrrolidone carboxylate | 0.3 |
| glycerin | 5.0 |
| hydroxyethyl cellulose | 0.1 |
| butyleneglycol | 5.0 |
| phenoxyethanol | 0.3 |
| water | 42.7 |
| total (wt %) | 100.0 |

INDUSTRIAL APPLICABILITY

The cosmetic composition of the present invention can be applied for various uses aiming at controlling and/or adding the color of the'skin or lips, and/or UV shielding.

Where a numerical limit or range is stated herein, the endpoints are included. Also, all values and subranges within numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A cosmetic composition, comprising:
(A) an N-acyl basic amino acid powder;
(B) an inorganic powder; and
(C) an oil material comprising silicone oil,
wherein:
said N-acyl basic amino acid powder consists of one or more N-medium-chain-acyl basic amino acids selected from the group consisting of $N^\varepsilon$-monohexanoyl lysine, $N^\varepsilon$-monooctanoyl lysine and $N^\varepsilon$-monodecanoyl lysine,
said N-acyl basic amino acid powder is present in an amount of 2.0 to 32.4 wt % based on the entire weight of said cosmetic composition,
said inorganic powder is present in an amount of 50.6 to 87.0 wt % based on the entire weight of said cosmetic composition,
said oil material is present in an amount of 1.0 to 47.4 wt % based on the entire weight of said cosmetic composition,
said N-acyl basic amino acid powder and said inorganic powder are present in a weight ratio (weight of said N-acyl basic amino acid powder:weight of said inorganic powder) of: 2.2:97.8 to 36.4:63.6, and
said N-acyl basic amino acid powder and said oil material are present in a weight ratio (weight of said N-acyl basic amino acid powder:weight of said oil material) of 15.4:84.6 to 74.7:25.3.

2. The cosmetic composition according to claim 1, wherein said N-acyl basic amino acid powder exhibits an internal frictional angle of 10.0 to 17.0 degrees.

3. The cosmetic composition according to claim 1, wherein said N-acyl basic amino acid powder consists of $N^e$-monooctanoyl lysine.

4. The cosmetic composition according to claim 1, which is a solid cosmetic.

5. The cosmetic composition according to claim 1, wherein said inorganic powder comprises talc.

6. A method of controlling the color of the skin or lips and/or adding color to the skin or lips, comprising applying a cosmetic composition according to claim 1 to the skin or lips of a subject in need thereof.

7. A method of UV shielding of skin, comprising applying a cosmetic composition according to claim 1 to the skin of a subject in need thereof.

* * * * *